United States Patent

Vedage et al.

Patent Number: 5,545,756
Date of Patent: Aug. 13, 1996

[54] HYDROGENATION OF AROMATIC AMINES USING MIXED METAL OXIDE SUPPORT

[75] Inventors: Gamini A. Vedage, Bethlehem; John N. Armor, Orefield, both of Pa.

[73] Assignee: Air Products and Chemicals, Inc., Allentown, Pa.

[21] Appl. No.: 306,069

[22] Filed: Sep. 14, 1994

[51] Int. Cl.⁶ ............................................. C09C 209/72
[52] U.S. Cl. ........................................ 564/450; 564/451
[58] Field of Search .................................... 564/450, 451

[56] References Cited

U.S. PATENT DOCUMENTS

| | | | |
|---|---|---|---|
| 2,511,028 | 6/1950 | Whitman | 260/563 |
| 2,606,924 | 8/1952 | Whitman | 260/563 |
| 2,606,925 | 8/1952 | Whitman | 260/563 |
| 2,606,928 | 8/1952 | Barkdoll et al. | 260/563 |
| 3,591,635 | 7/1971 | Farrissey et al. | 260/563 B |
| 3,636,108 | 1/1972 | Brake | 260/563 D |
| 3,644,522 | 2/1972 | Brake et al. | 260/563 D |
| 3,697,449 | 10/1972 | Brake | 252/474 |
| 3,856,862 | 12/1974 | Chung et al. | 260/563 B |
| 4,376,724 | 3/1983 | Mita et al. | 252/460 |
| 4,448,995 | 5/1984 | Allen | 564/451 |
| 4,754,070 | 6/1988 | Casey et al. | 564/451 |
| 4,960,941 | 10/1990 | Vedlage et al. | 564/450 |
| 5,026,914 | 6/1991 | Jenkins et al. | 564/450 |

Primary Examiner—Brian M. Burn
Attorney, Agent, or Firm—Russell L. Brewer; Mary E. Bongiorno

[57] ABSTRACT

This invention relates to an improved hydrogenation process wherein aromatic amines are hydrogenated to their ring hydrogenated counterparts using an improved rhodium catalyst. The aromatic amines are represented by the formulas:

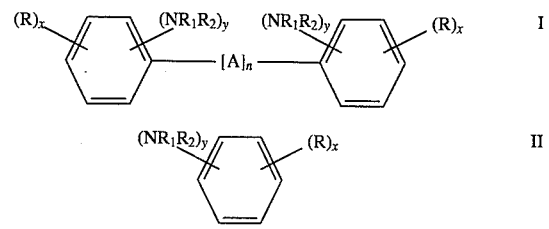

wherein R is hydrogen or $C_{1-6}$ aliphatic, $R_1$ and $R_2$ are hydrogen or $C_{1-6}$ aliphatic, A is $C_{1-4}$ alkyl, n is 0 or 1, x is 1–3 and y is 1 to 2 except the sum of the y groups in Formula I excluding A may be 1.

The rhodium catalyst is carried on a support selected from the group consisting of $TiAl_2O_5$, $TiSrO_3$ and $TiSiO_4$.

20 Claims, No Drawings

HYDROGENATION OF AROMATIC AMINES USING MIXED METAL OXIDE SUPPORT

FIELD OF THE INVENTION

This invention relates to a process for the hydrogenation of aromatic amines using a rhodium containing catalyst supported on a mixed titanium or strontium metal oxide support.

BACKGROUND OF THE INVENTION

There is substantial literature in the art with respect to the hydrogenation of aromatic amines, e.g., methylenedianiline to produce 4,4'-methylenedi(cyclohexylamine) often referred to as PACM.

Some of the early hydrogenation work to produce PACM was done by Whitman and Barkdoll, et al. and their work is set forth in a series of U.S. patents, e.g., U.S. Pat. Nos. 2,511,028; 2,606,924; 2,606,925; and 2,606,928. Basically the processes described in these patents involve the hydrogenation of methylenedianiline at pressures in excess of 200 psig, preferably in excess of 1,000 psig, at temperatures within a range of 80° to 275° C. utilizing a ruthenium catalyst for the hydrogenation. The hydrogenation is carried out under liquid phase conditions by using an inert organic solvent in the hydrogenation process. Examples of ruthenium catalysts utilized for the hydrogenation process include ruthenium oxides such as ruthenium sesquioxide and ruthenium dioxide.

Brake, et al. continued in the development of processes for manufacturing PACM by hydrogenating methylenedianiline. They found that if the ruthenium was carried upon a support and the support was alkali-moderated, the catalyst was much more active and catalytically effective in producing the desired hydrogenated PACM product. Alkali moderation was effected by contacting the catalyst and support with alkali metal hydroxide or an alkoxide; also, such alkali moderation of the catalyst could be effected prior to hydrogenation or in situ during the hydrogenation.

Representative patents showing the utilization of alkali moderated ruthenium catalysts to hydrogenate methylenedianiline include U.S. Pat. Nos. 3,636,108; 3,644,522; and 3,697,449. Alkali metal and alkaline earth metal nitrates and sulfates have similarly been shown effective in U.S. Pat. No. 4,448,995 under high pressure (4000 psia) hydrogenation conditions. Representative supports in the '449 patent include bauxite, periclase, zirconia, titania, diatomaceous earth, etc.

Other catalysts have been utilized for the hydrogenation of methylenedianiline and examples are shown in U.S. Pat Nos. 3,591,635 and 3,856,862. Both disclose the use of a rhodium component as a catalytic material and each require the use of an aliphatic alcohol as a solvent. The rhodium is alkali moderated using ammonium hydroxide as a pretreatment or by carrying out the reaction in the presence of ammonia. European application 66,212 discloses the use of rhodium on alumina to obtain 15–40% trans,transisomer ratio but again the pressures are high (4000 psia).

U.S. Pat. No. 4,376,724 discloses a catalyst with rhodium present in the surface layer of particles of silica or titania which is alleged as being suited for the synthesis of oxygen containing compounds and various hydrogenation reactions including the nuclear hydrogenation of aromatic compounds and in the hydrogenation of unsaturated bonds of olefins, nitriles, etc. The catalyst is prepared by dipping the support into an aqueous solution of a water soluble rhodium salt adjusted to a specific pH followed by drying and reduction. The supports include silica or titania as a single component.

U.S. Pat. Nos. 4,960,941 and 5,026,914 disclose a process for the hydrogenation of aromatic amines utilizing a catalyst comprising rhodium on titania or zirconia. To enhance attrition resistance titania and/or zirconia chemically bound to silica was used as a support for the rhodium.

U.S. Pat. No. 4,754,070 discloses a process for hydrogenation methylenediamiline using a mixed metal catalyst of rhodium and ruthenium carried of a variety of supports, alumina and diatomaceous earth.

SUMMARY OF THE INVENTION

This invention relates to an improved catalytic process for producing aromatic amines such as 4,4'-methylenedi(cyclohexylamine) (PACM) by the catalytic hydrogenation of such aromatic amines to produce their hydrogenated counterparts. The improvement in the hydrogenation process comprises using a catalytic system comprising rhodium supported on a mixed metal support selected from the group consisting of $TiAl_2O_5$, $TiSiO_4$ and $TiSrO_3$. Preferably the catalyst comprises rhodium and ruthenium wherein the weight ratio of rhodium to ruthenium, calculated on metal content, is from 1 to 12:1. In addition, the invention pertains to the catalyst.

There are several advantages associated with this process and catalyst. These include:

an ability to use the catalyst for continued periods of time with only modest maintenance or regeneration; and a catalyst having excellent attrition resistance in liquid phase hydrogenation reactions.

DETAILED DESCRIPTION OF THE INVENTION

This invention relates to an improvement in the conventional ring hydrogenation of aromatic amines and to the catalysts and these amines are represented by the formulas:

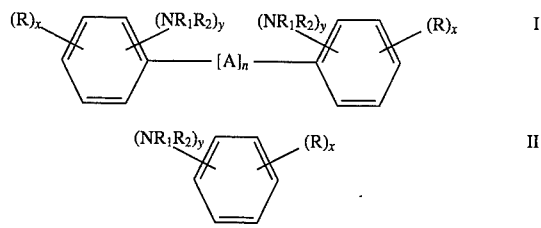

wherein R is hydrogen or $C_{1-6}$ aliphatic, $R_1$ and $R_2$ are hydrogen, or $C_{1-6}$ aliphatic, A is $C_{1-4}$ alkyl, n is 0 or 1, x is 1–3 and y is 1–2 except the sum of the y groups in Formula I excluding A may be 1. Where R is hydrogen then the ring is unsubstituted. By the practice of this invention, one is able to selectively produce a ring hydrogenated reaction product in high selectivity with excellent reaction rates.

The aromatic amines useful in the practice of the process can be bridged polynuclear aromatic amines or mononuclear aromatic amines. These can be substituted with various substituents such as aliphatic groups containing from 1–6 carbon atoms. Further, the amine group can be substituted with aliphatic groups such as alkyl or alkanol groups resulting in secondary and tertiary amine substituents. Examples of bridged aromatic amines include methylenedianilines such as bis(para-aminophenyl) methane and bis(para-amino-2-methylphenyl) methane; toluidine; bis(diaminophenyl)methane; α,α'-bis(4-aminophenyl-para-diisopropyl benzene(bisaniline P), bis(diaminophenyl)propane (bisaniline A); biphenyl, N-$C_{1-4}$-aliphatic derivatives and N,N'$C_{1-4}$ aliphatic secondary and tertiary amine derivatives of the above bridged aromatic amines. Examples of mononuclear aromatic amines include 2,4- and 2,6-toluenediamine, aniline, butenyl-aniline derivatives, 1-methyl-3,5-diethyl-2, 4- and 2,6-diaminobenzene (diethyltoluenediamine); monoisopropyltoluenediamine, diisopropyltoluenediamine, tert-butyl-2,4- and 2,6-toluenediamine, cyclopentyltoluenediamine, ortho-tolidine, ethyl toluidine, xylenediamine, mesitylenediamine, phenylenediamine and the N and N,N'$C_{1-4}$ aliphatic secondary and tertiary amine derivatives of the mononuclear aromatic monoamines and mononuclear aromatic diamines.

As with conventional processes the hydrogenation process usually is carried out under liquid phase conditions, such liquid phase conditions being maintained typically by carrying out the hydrogenation in the presence of a solvent. Although as reported in the art, it is possible to effect reaction in the absence of a solvent, the processing usually is much simpler when a solvent is employed. Representative solvents suited for hydrogenation of aromatic amines include saturated aliphatic and alicyclic hydrocarbons such as cyclohexane, hexane, and cyclooctane; low molecular weight alcohols, such as methanol, ethanol, isopropanol; and aliphatic and alicyclic hydrocarbon ethers, such as n-propyl ether, isopropyl ether, n-butyl ether, amyl ether, tetrahydrofuran, dioxane, and dicyclohexylether. Tetrahydrofuran is preferred. Although in some processes water can be used as a cosolvent, it is preferred that the system be maintained in an anhydrous state or at least maintained so that the water concentration is less than 0.5% by weight. Water, when present in the system, tends to increase the amount of by-product alcohols and heavy condensation products during the hydrogenation process and tends to deactivate the catalyst system.

When a solvent is used, it can be used in concentrations as low as 50% by weight based upon the aromatic amine introduced into the reaction and typically the solvent is used at levels from about 75 to about 200% by weight of the starting compound. Under some circumstances solvent amounts as high as 1000 to 2000% based upon the weight of aromatic amine are used. In contrast to the prior art hydrogenation processes, particularly for bridged anilines, hydrogen partial pressures can range from about 200 to 4000 psig, preferably no higher than 2500 psig and typically can be as low as from about 700 to 1500 psig, which may be preferred for lower equipment and operating costs. When the pressure is raised toward the upper end of the operating range, higher reaction rates may be achieved.

The ability to ring hydrogenate aromatic amines, and particularly crude methylenedianiline containing oligomers and other known catalyst poisons at low hydrogen partial pressures and obtain high conversion with excellent reaction rates while minimizing loss to attrition, is achieved by the utilization of a specific catalyst system. The catalyst utilized in the hydrogenation process comprises rhodium supported on a mixed metal support selected from the group consisting of $TiAl_2O_5$, $TiSiO_4$ and $TiSrO_3$.

Preparation of the $TiAl_2O_5$, the $TiSiO_4$ and $TiSrO_3$ supports is conducted in accordance with conventional procedures. Typically this involves coprecipitation of metal salts in aqueous solutions followed by drying and calcining. The catalyst then is prepared by precipating the catalyst metal onto the support. For example, a rhodium catalyst is prepared by precipitating rhodium salts, such as the nitrates dissolved in water, on a support and the resulting impregnated support dried and calcined.

The rhodium salt is combined with the mixed metal support in an amount based upon its weight as metal, to provide a ratio of about 0.1 to 25 weight parts rhodium per 100 weight parts of support, preferably 3 to 8 weight parts rhodium per 100 weight parts support. With respect to the preferred catalyst, ruthenium is added to the catalyst with the rhodium to ruthenium weight ratio being from about 1–12:1, preferably 4–8 weight parts rhodium/weight part ruthenium on the support.

In the past, to maintain high activity of the catalyst system in the hydrogenation process it was proposed that the rhodium and ruthenium component, if present, be alkali moderated. Alkali moderation techniques to produce the catalyst system are well known and the techniques disclosed in U.S. Pat. No. 3,636,108 for the alkali moderation of ruthenium can be utilized for rhodium. Such method is incorporated by reference. However, as previously noted, the mixed metal oxide support apparently does not need significant alkali metal hydroxide moderation as do other supports, e.g., alumina. Typically, such alkali moderation involves the treatment of the catalyst and support material with an alkali metal hydroxide such as, sodium, lithium or potassium hydroxide or alkali metal alkoxide such as sodium, lithium, or potassium methoxide or ethoxide in an amount to provide from 0.1 to 15% by weight of a basic metal compound calculated as alkali metal. Often, alkali moderation of the catalyst is done prior to reduction of the catalyst with aqueous dilute alkali metal hydroxide during or following metal deposition on the chosen support. Alkali moderation can also be accomplished, in situ, i.e., during hydrogenation by adding alkali metal hydroxide, e.g., lithium hydroxide, alkali metal alkoxide or by the addition of ammonia to the reaction medium.

The following examples are intended to illustrate various embodiments of the invention and all parts and percentages given are weight parts or weight percents unless otherwise specified.

EXAMPLE 1

Preparation of 4% Rh/$TiAl_2O_5$ ($TiO_2$:$Al_2O_3$=1:1) Catalyst a. Preparation of $TiAl_2O_5$ Support 14 g of pseudo Boehmite (~30% water) was added to 200 g of isopropanol. To this solution was added 34 g of Ti-isopropoxide. The solution was then evaporated to dryness. The support precursor was then heated to 650° C. for 16 hours, thus obtaining the final support.

b. Preparation of 4% Rh/$TiAl_2O_5$ ($TiO_2$:$Al_2O_3$=1:1) Catalyst

To 4.0 g Rh($NO_3$)$_3$ (10% Rh) solution, was added 10 g of the above support and the suspension mixed. The catalyst was dried overnight at 100° C. and calcined at 400° C. for 3 hours in air to obtain the final catalyst.

EXAMPLE 2

High Temperature Treated 4% Rh/$TiAl_2O_5$ ($TiO_2$:$Al_2O_3$=1:1)

a. Preparation of High Temperature Treated $TiAl_2O_5$ Support 14 g of pseudo Boehmite (~30% water) was added to 200 g of isopropanol. To this solution was added 34 g of Ti-isopropoxide; the solution was then evaporated to dryness. The support precursor was then heated to 900° C. for 16 hours.

b. Preparation of 4% Rh/TiAl$_2$O$_5$ (TiO$_2$:Al$_2$O$_3$=1:1) Catalyst

To 4.0 Rh(NO$_3$)$_3$ (10% Rh) solution, was added 10 g of support and mixed the suspension well. The catalyst was dried overnight at 100° C. and calcined at 400° C. for 3 hours in air to obtain the final catalyst.

EXAMPLE 3

Preparation of 4% Rh/TiAl$_2$O$_5$ (TiO$_2$:Al$_2$O$_3$=1:9) Catalyst 31 g of TiAl$_2$O$_5$ (1:9) was first calcined at 650° C. for 18 hours. Then, to 4.0 g Rh(NO$_3$)$_3$ [10% Rh] solution, was added 10 g of the above calcined support and the suspension mixed. The catalyst was dried overnight at 110° C. and calcined at 400° C. for 3 hours in air to obtain the final catalyst.

EXAMPLE 4

Preparation of 4% Rh/TiAl$_2$O$_5$ (TiO$_2$:Al$_2$O$_3$=9:1) Catalyst Extended Calcination a. Preparation of TiAl$_2$O$_5$ (9:1) Support 2.8 g of pseudo boehmite was mixed with 62.2 g Ti-isopropoxide. This mixture was added to an aqueous ammonia solution containing 60 g of NH$_4$OH and 100 g of DI water. The whole mixture was heated to 80° C. for 2 hours and then water and ammonia reevaporated in a 110° C. oven. The catalyst support precursor was then calcined at 650° C. for 18 hours.

b. Preparation of 4% Rh/TiAl$_2$O$_5$ (TiO$_2$:Al$_2$O$_3$=9:1) Catalyst

To 4.0 g Rh(NO$_3$)$_3$ (10% Rh) solution, was added 10 g of support and the suspension mixed. The catalyst was dried overnight at 100° C. and calcined at 400° C. for 3 hours in air to obtain the final catalyst.

EXAMPLE 5

Preparation of 4% Rh/TiAl$_2$O$_5$ (TiO$_2$:Al$_2$O$_3$=1:1)—Alkoxide Prep a. Preparation of TiAl$_2$O$_5$ (1:1) Support—Alkoxide Prep 66.5 g of Al(OC$_4$H$_9$)$_3$ and 43 g Ti(OC$_3$H$_7$)$_4$ were mixed together. This mixed metal alkoxide solution then was added to an NH$_4$OH solution containing 300 g deionized (DI) water and 50 g NH$_4$OH. The mixture was stirred for a half hour and then allowed to settle overnight. The precipitate was separated by filtering. The precipitate was calcined at 650° C. six hours to produce the final support.

b. Preparation of 4% Rh/TiAl$_2$O$_5$ (TiO$_2$:Al$_2$O$_3$=1:1) Catalyst Alkoxide To 4.0 g Rh(NO$_3$)$_3$ (10% Rh) solution, was added 10 g of 10a support and the suspension mixed. The catalyst was dried overnight at 100° C. and calcined at 400° C. for 3 hours in air to obtain the final catalyst.

EXAMPLE 6

Preparation of 3% Rh/TiAl$_2$O$_5$ (TiO$_2$:Al$_2$O$_3$=1:1) Catalyst

To 3.0 g Rh(NO$_3$)$_3$ (10% Rh) solution, was added 10 g of the Example 1a support and the suspension mixed. The catalyst was dried overnight at 100° C. and calcined at 400° C. for 3 hours in air to obtain the final catalyst.

EXAMPLE 7

Preparation of 2% Rh/TiAl$_2$O$_5$ (TiO$_2$:Al$_2$O$_3$=1.1) Catalyst

To 2.0 g Rh(NO$_3$)$_3$ (10% Rh) solution, was added 10 g of the Example 1a support and the suspension mixed. The catalyst was dried overnight at 100° C. and calcined at 400° C. for 3 hours in air to obtain the final catalyst.

EXAMPLE 8

Preparation of 4.5% LiOH doped 4% Rh/TiAl$_2$O$_5$ (TiO$_2$:Al$_2$O$_3$=1.1) Catalyst To 7 g of the Example 1a support was added 0.55 g LiOH.H$_2$O dissolved in 7.5 g DI water. This mixture was placed in an oven at 400° C. for 1 hr. 2 g of Rh(NO$_3$)$_3$ (10% Rh) solution was added to 5 g of the above 1a support and after drying at 100° C. it was calcined at 400° C. for 3 hours to obtain the final catalyst.

EXAMPLE 9

Preparation of 3.5% LiOH doped 4% Rh/TiAl$_2$O$_5$ Catalyst

The same procedure as in Example 8 was followed with the exception of that 0.37 g LiOH.H$_2$O were added to provide the 3.5% LiOH level.

EXAMPLE 10

Preparation of 4% Rh/TiSrO$_3$ (SrO:TiO$_2$=1.1) Catalyst Calcined at 700° C.

a. Preparation of TiSrO$_3$ Support (SrO:TiO$_2$=1:1)

To 24 g of Ti-isopropoxide was added a solution of Sr(NO$_3$)$_2$ (12.5 g dissolved in 200 g DI water). The pH of the solution was increased to 9.5 by adding NH$_4$OH. The precursor was separated by filtering and then it was dried at 100° C. and calcined at 700° C. for 12 hours.

b. Preparation of 4% Rh/TiSrO$_3$ catalyst

To 4.0 g Rh(NO$_3$)$_3$ (10% Rh) solution, was added log of support and the suspension mixed well for 0.1 hours. The catalyst was dried overnight at 100° C. and calcined at 400° C. for 3 hours in air to obtain the final catalyst.

c. Preparation of 2% Rh/TiSrO$_3$ catalyst

To 2.0 g Rh(NO$_3$)$_3$ (10% Rh) solution, was added 10 g of support and the suspension mixed well for 0.1 hours. The catalyst was dried overnight at 100° C. and calcined at 400° C. for 3 hours in air to obtain the final product.

EXAMPLE 11

Preparation of 4%Rh/TiSrO$_3$ (SrO:TiO$_2$=1:1) Calcined at 400° C.

a. Preparation of the TiSrO$_3$ (SrO:TiO$_2$=1:1) support

To 24 g of Ti-isopropoxide was added a solution of $Sr(NO_3)_2$ (12.5 g dissolved in 200 g DI water). The pH of the solution was increased to 9.5 by adding $NH_4OH$. The precursor was separated by filtering and then it was dried at 100° C. and calcined at 400° C. for 12 hours.

b. Preparation of 4% $Rh/TiSrO_3$ ($SrO:TiO_2=1:1$) catalyst

To 4.0 g $Rh(NO_3)_3$ (10% Rh) solution, was added 10 g of support and the suspension mixed well for 0.1 hours. The catalyst was dried overnight at 100° C. and calcined at 400° C. for 3 hours in air to obtain the final catalyst.

EXAMPLE 12

Preparation of 4% $Rh/TiSrO_3$ ($SrO:TiO_2=1:9$) Catalyst a. Preparation of $TiSrO_3$ ($SrO:TiO_2=1:9$) support To 68.2 g of Ti-isopropoxide was added a solution of $Sr(NO_3)_2$ (12.7 g dissolved in 200 g DI water). The pH of the solution was increased to 9.5 by adding $NH_4OH$. The precursor was separated by filtering, dried at 100° C. and calcined at 700° C. for 12 hours.

b. Preparation of 4% $Rh/TiSrO_3$ ($SrO:TiO_2=1:9$) Catalyst

To 4.0 g $Rh(NO_3)_3$ (10% Rh) solution, was added log of support and mixed. The catalyst was dried overnight at 100° C. and calcined at 400° C. for 3 hours in air to obtain the final catalyst.

EXAMPLE 13

Preparation of 4% Rh/SrO a. Preparation of SrO Support 80 g of $Sr(NO_3)_3$ was added to 200 g DI water and to that was added 40 g of $(NH_4)_2CO_3$. The white precipitate was separated by filtering and then it was dried and calcined at 700° C. overnight.

b. Preparation of 4%Rh/SrO Catalyst

To 4.0 g $Rh(NO_3)_3$ (10% Rh) catalyst solution was added log of the above support and the suspension mixed. The catalyt was dried overnight at 100° C. and calcined at 400° C. for 3 hours in air to obtain the final catalyst.

EXAMPLE 14

4% $Rh/TiSiO_4$ ($SiO_2:TiO_2=1:1$) Made from Alkoxides a. Preparation of Support To 34.7 g of $Si(OC_2H_5)_4$ was added 47.3 g of titanium isopropoxide and the solutions mixed. This solution was added to a 350 g of $NH_4OH$ solution (50 g of $NH_4OH$ dissolved in 300 g of DI water) while stirring. The precipitate was separated by filtering and then it was dried overnight in a 100° C. oven. Finally, this was calcined at 650° C. for 16 hours to obtain the final support.

5b. Preparation of 4% $Rh/TiSiO_4$ ($SiO_2:TiO_2=1:1$) Catalyst

To 2.0 g $Rh(NO_3)_3$ (10%Rh) solution, was added 5 g of the above support the suspension mixed. The catalyst was dried overnight at 100° C. and calcined at 400° C. for 3 hours in air to obtain the final catalyst.

EXAMPLE 15

4% $Rh/TiSiO_4$ ($TiO_2:SiO_2=1:1$) Starting with Collidal Silica a. Preparation of Support 30 g of a commercial collidal silica (40% silica) was mixed with 57 g of titanium isopropoxide and log of DI water and the product was mixed well. The mixture was evaporated to dryness at 110° C. and the product was calcined at 650° C. for 16 hours.

b. Preparation of 4% $Rh/TiSiO_4$ ($TiO_2:SiO_2=1:1$) Catalyst

To 2.0 g $Rh(NO_3)_3$ (10%Rh) was added 5 g of support and the suspension mixed. The catalyst was dried overnight at 100° C. and calcined at 400° C. for 3 hours in air to obtain the final product.

EXAMPLE 16

Preparation of 4% $Rh/TiO_2$(Isopropoxide Prep.)

a. Preparation of Support

To 80 g Ti-isopropoxide was added 300 ml DI water while stirring and allowed the mixture to dry in air in a large porcelain dish. The dried precursor was calcined at 650° C. for 5 hours to prepare the catalyst support.

b. Preparation of 4% $Rh/TiO_2$ (Isopropoxide Prep.)

To 10 g of the above support added 4 g of $Rh(NO_3)_3$ (10% Rh) and the solids mixed well. The catalyst was dried overnight at 100° C. and calcined at 400° C. for 3 hours in air to obtain the final catalyst.

COMPARATIVE EXAMPLE 17

4% $Rh/SiO_2$

To 4.0 g $Rh(NO_3)_3$ (10% Rh) solution, was added 10 g of Davidson 57 $SiO_2$ and the suspension mixed well. The catalyst was dried overnight at 100° C. and calcined at 400° C. for 3 hours in air to obtain the final catalyst.

EXAMPLE 18

4% $Rh/ZrAl_2O_5$ ($ZrO_2:Al_2O_3=1:1$)

a. Preparation of Support

To a mixture of 36.4 g of $Zr(OC_3H_7)_4$ and 27.4 g of $Al(OC_4H_9)_3$, 100 g of DI water was added and the mixture was stirred together for 20 minutes. The mixture was evaporated to dryness at 110° C. and the product was calcined at 650° C. for 16 hours to obtain the final product.

b. Preparation of 4% $Rh/ZrAl_2O_5$ ($ZrO_2:Al_2O_3=1:1$) Catalyst

To 2.0 g $Rh(NO_3)_3$ (10% Rh) was added 5 g of support and mixed the suspension well. The catalyst was dried overnight at 100° C. and calcined at 400° C. for 3 hours in air to obtain the final product.

COMPARATIVE EXAMPLE 19

4% $Rh/ZrSiO_4$($ZrO_2:SiO_2=1:1$)

a. Preparation of Support

To a mixture of 33.2 g of $Zr(OC_3H_7)_4$ and 20.8 g $Si(OC_2H_5)_4$, 80 g of DI water was added and the mixture was stirred together for 20 minutes. The mixture was dried in a 110° C. oven and the product was calcined at 650° C. for 16 hours to obtain the final product.

b. Preparation of 4% Rh/ZrSiO$_4$ (ZrO$_2$:SiO$_2$=1:1) Catalyst

To 2.0 g Rh(NO$_3$)$_3$ (10% Rh) was added 5 g of support and the suspension mixed. The catalyst was dried overnight at 100° C. and calcined at 400° C. for 3 hours in air to obtain the final product.

COMPARATIVE EXAMPLE 20

4% Rh/ZrO$_2$ 4.0 g Rh(NO$_3$)$_3$ (10% Rh) was added to 10 g of ZrO$_2$ and the suspension mixed well. The catalyst was dried overnight at 100° C. and calcined at 400° C. for 3 hours in air to obtain the final product.

EXAMPLE 21

Hydrogenation of Methylenedianiline

In the following series of runs a conventional procedure for effecting the hydrogenation of methylenedianiline was utilized, the purpose being for measuring the activity and selectivity of the catalyst. More particularly, a 300 cc autoclave was charged with preselected catalysts at preselected weight percent of the catalyst and 125 g of THF. Following purging and pressurizing with hydrogen, the autoclave was heated to reaction temperature and pressurized to reaction pressure for 2 hours. It was then cooled, vented and the THF was removed under nitrogen. 125 g of 50% MDA in THF was added to the autoclave. Following purging and pressurizing with hydrogen, the autoclave was heated to reaction temperature. A total pressure of 850 psi was maintained from a ballast tank. The catalyst was readily recovered from the reaction mixture with ease. The reaction product was analysed. The conditions and results are set forth in Tables 1 and 2.

The following properties of the above catalysts were studied. (a) Effect of Al$_2$O$_3$:TiO$_2$ ratio. (b) Effect of rhodium loading. (c) Effect of calcination temperature. (d) Methods of minimizing secondary amines.

TABLE 1

Hydrogenation of 50% MDA/THF at 180° C., 850 psi pressure
Catalyst loading of 1.5 wt% based on the weight of MDA

| Run | Catalyst[b] | Use | T95[a] (or TEND) (min) | Conv (%) | PACM (%) | t/t (%) | Half PACM (%) | Deaminated Product (%) | PACM-Sec Amines % |
|---|---|---|---|---|---|---|---|---|---|
| 1 | 4% Rh/TiSrO$_3$ (1:1) Ex 10b | 1 | 224 | 98 | 79.2 | 16.8 | 3.6 | 2.2 | 15.0 |
| 1a | | 2 | 110 | 99 | 79.3 | 16.1 | 2.8 | 2.4 | 15.4 |
| 1b | | 3 | 110 | 99 | 81.4 | 17.7 | 1.4 | 2.1 | 15.1 |
| 2 | 2% Rh/TiSrO$_3$ (1:1) Ex 10c | 1 | 150 | 89 | 69.3 | 14.3 | 22.4 | 1.8 | 6.3 |
| 2a | | 2 | 150 | 96 | 80.2 | 15.4 | 8.7 | 1.8 | 9.3 |
| 3 | 4% Rh/TiSrO$_3$ (1:9) Ex 12 | 1 | 285 | 74 | 37.4 | 13.8 | 47.5 | 2.2 | 10.9 |
| 3a | | 2 | 135 | 99 | 83.4 | 17.1 | 2.4 | 2.0 | 12.2 |
| 4 | 4% Rh/TiSrO$_3$ (1:1) Ex 11 (calcined 400° C.) | 1 | 433 | 71 | 33.7 | 11.7 | 49.8 | 2.5 | 9.8 |
| 4a | | 2 | 150 | 68 | 29.7 | 13.3 | 51.7 | 2.6 | 9.5 |
| 5 | 4% Rh/SrO Ex 13 | 1 | 400 | 7 | 0.8 | 12.1 | 11.9 | 0.1 | 0.0 |
| 6 | 4% Rh/TiO$_2$ (isoprop.) Ex 16 | 1 | 135 | 95 | 73.2 | 13.9 | 9.5 | 2.6 | 14.7 |
| 6a | | 2 | 140 | 96 | 74.7 | 13.6 | 8.7 | 2.6 | 15.6 |

Conv refers to conversion of methylenedianiline in weight percent.
Deaminated product refers to deaminated methylenedicyclohexylamine derivatives.
PACM Secondary amines refers to secondary amines of PACM.
[a]Time for 95% conversion if the conversion >95%. TEND is the time for a given conversion if it is <95%.
[b]5% Ru/Al$_1$O$_3$ was added such that the Rh:Ru ratio was 10:1.

TABLE 2

Hydrogenation of 50% MDA/THF at 180° C.
850 psi pressure at a catalyst loading of 1.5 wt %

| Run | Catalyst[b] | Use | T95[a] or (TEND) (min) | Conv (%) | PACM (%) | t/t (%) | Half PACM (%) | Deamin. Prod. (%) | PACM Sec. Amines % |
|---|---|---|---|---|---|---|---|---|---|
| 1. | 4% Rh/TiAl$_2$O$_5$ (1:1) Ex 1 | 1 | 80 | 100 | 78.9 | 14.7 | 0.4 | 1.6 | 18.9 |
| 1a. | | 2 | 55 | 100 | 80.0 | 15.5 | 0.0 | 1.6 | 18.3 |
| 2. | 4% Rh/TiAl$_2$O$_5$ (9:1) Ex 4 | 1 | 110 | 99 | 77.4 | 16.2 | 1.2 | 2.1 | 19.3 |
| 2a. | | 2 | 75 | 99 | 77.2 | 14.9 | 2.5 | 2.1 | 18.3 |

TABLE 2-continued

Hydrogenation of 50% MDA/THF at 180° C.
850 psi pressure at a catalyst loading of 1.5 wt %

| Run | Catalyst[b] | Use | T95[a] or (TEND) (min) | Conv (%) | PACM (%) | t/t (%) | Half PACM (%) | Deamin. Prod. (%) | PACM Sec. Amines % |
|---|---|---|---|---|---|---|---|---|---|
| 3. | 4% Rh/TiAl$_2$O$_5$ 1:9 Ex 3 | 1 | 100 | 99 | 71.4 | 13.3 | 1.7 | 1.6 | 25.3 |
| 3a. | | 2 | 110 | 100 | 68.8 | 13.9 | 0.8 | 1.5 | 28.8 |
| 4. | 3% Rh/TiAl$_2$O$_5$ 1:1 Ex 6 | 1 | 180 | 98 | 76.7 | 13.8 | 4.7 | 1.7 | 16.9 |
| 4b. | | 2 | 85 | 99 | 78.0 | 14.6 | 1.7 | 1.6 | 18.7 |
| 5. | 2% Rh/TiAl$_2$O$_5$ (1:1) Ex 7 | 1 | 220 | 96 | 69.1 | 14.2 | 8.8 | 1.5 | 20.7 |
| 5b. | | 2 | 150 | 100 | 75.0 | 15.2 | 1.1 | 1.3 | 22.7 |
| 6. | 2% Rh/TiAl$_2$O$_5$[c] 1:1 | 1 | 255 | 96 | 71.4 | 15.8 | 8.5 | 1.6 | 18.5 |
| 6b. | | 2 | 135 | 100 | 77.0 | 16.6 | 0.7 | 1.5 | 20.8 |
| 7. | 4% Rh/TiAl$_2$O$_5$[c] 1:1 Ex 2 | 1 | 107 | 99 | 75.8 | 14.0 | 1.5 | 1.9 | 20.8 |
| 7b. | | 2 | 85 | 99 | 77.4 | 13.7 | 1.6 | 1.9 | 19.1 |
| 8. | 4% Rh/TiAl$_2$O$_5$[d] 1:1 | 1 | 65 | 99 | 71.5 | 14.1 | 2.7 | 1.7 | 24.1 |
| | | 2 | 55 | 99 | 71.3 | 14.4 | 2.1 | 1.7 | 24.9 |
| 9. | 4% Rh/TiO$_2$ Ex 16 | 1 | 135 | 95 | 73.2 | 13.6 | 9.5 | 2.6 | 14.7 |
| | | 2 | 140 | 96 | 74.7 | 13.6 | 8.7 | 2.6 | 15.6 |
| 10. | 4% Rh/Al$_2$O$_3$[f] | 1 | 190 | 99 | 94.1 | 19.4 | 1.2 | 1.1 | 3.6 |
| | | 2 | 150 | 99 | 94.3 | 17.9 | 0.7 | 1.1 | 4.0 |
| 11. | 4% Rh/Al$_2$O$_3$[f] + 4% Rh/TiO$_2$ (Ex 16) (1:1) | 1 | 160 | 89 | 64.4 | 12.3 | 20.7 | 1.6 | 12.7 |
| | (physical mixture) | 2 | 160 | 89 | 62.7 | 12.0 | 22.5 | 1.8 | 12.4 |

[a]Same as Tbale 1.
[b]Same as Table 1.
[c]Support calcined at 900° C. instead of 650° C.
[d]Support made with Ti and Al alkoxides instead of Ti-isopropoxide and pseudoboehmide.
[e]Prepared with Rh$_6$(CO)$_6$ instead of the standard Rh(NO$_3$)$_3$. Preparation technique same as Example 7.
[f]Commercial 4% Rh/Al$_2$O$_3$ catalyst.

As shown in Table 1, the 4% Rh/TiSrO$_3$ (TiO$_2$:SrO=1.1 - 700° C. calcined) is very active for MDA hydrogenation. One surprising feature with most of the catalysts is that they become more active with the first use. Presummably activation continues throughout the first run. This catalyst was characterized and found that the major support phase was TiSrO$_3$ with a total surface area (TSA) of 8 m$^2$/g and a metal surface area (MSA) of 1.7 m$^{2/g}$. The 4% Rh/TiSrO$_3$ catalyst with 8 m$^2$/g total surface area (TSA) has an activity similar to a 4% Rh/Al$_2$O$_3$ commercial catalyst (TSA=100 m$^2$/g; MSA=8 m$^2$/g) for MDA hydrogenation (see Table 2). These results clearly show that the rhodium on the TiSrO$_3$ support is highly active. Further it shows that the support is uniquely very active to catalyze hydrogenation even at very low metal and total surface areas.

The results of the study show the 4% Rh/SrO (Run 5 of Table 1) is ineffective for MDA hydrogenation. The T95 (time for 95% conversion) for 4% Rh/TiSrO$_3$ with SrO:TiO$_2$ ratios of 1:1 and 1:9 are 110 min and 135 min respectively, (Runs 1a, 1b, and 3a of Table 1). The T95 for 4% Rh/TiO$_2$ catalyst for MDA hydrogenation is 135 min (Run 6). Therefore, it appears that the support material, TiSrO$_3$ (SrO:TiO$_2$= 1:1), which is more active than SrO and TiO$_2$ supported rhodium catalysts for the hydrogenation of aromatic amines. The synergism in activity with the Rh/TiSrO$_3$ catalysts is probably due to the unique nature of TiSrO$_3$ surface and its ability to disperse rhodium on it. Further, the surface might have some special properties which would accelerate the activation of hydrogen by rhodium. The secondary amines, the deaminated product and the t/t isomer content of the Rh/TiSrO$_3$ catalyst are similar to those obtained with the Rh/TiO$_2$ catalyst.

As shown in Table 1, 2% Rh/TiSrO$_3$ (50/50 - 700° C.) is also very active for MDA hydrogenations and has an activity similar to 4% Rh/TiO$_2$ catalyst. These results show that the 2% Rh/TiSrO$_3$ catalyst has similar activity to 4% Rh/TiO$_2$ catalyst, yet with half the amount of rhodium.

Table 2 gives the results of the effect of TiO$_2$:Al$_2$O$_3$ ratio on catalytic activity of 3–4% Rh/TiAl$_2$O$_5$ catalyst for the hydrogenation of MDA. The results of Table 2 shows that the catalytic support (TiAl$_2$O$_5$) has a higher activity, for MDA hydrogenation, than either Al$_2$O$_3$ or TiO$_2$ supported rhodium catalysts or physical mixtures thereof. T95 values to 95% conversion directly relate to catalyst activity. The T95 for MDA hydrogenation with 4% Rh/TiO$_2$ (or Al$_2$O$_3$) catalyst is about 135–150 min (Run 6, Table 1). With the mixed 4% Rh/TiAl$_2$O$_5$ catalysts, the T95 is 110 min when the ratio of TiO$_2$:Al$_2$O$_3$ is 1:9 (Run 2 of Table 2), and the T95 is 75 min when that ratio is 9:1 (Run 3 of Table 2). A TiO$_2$:Al$_2$O$_3$ ratio of 1.1 produces a support which gives a maximum in activity (or minimum T95) with a T95 of 55 min (Table 2). This is one of the fastest reactions that has been observed for the hydrogenation of MDA.

Table 2 also gives the activity of a physical mixture of 4% Rh/Al$_2$O$_3$ and 4% Rh/TiO$_2$ catalyst (1:1) for the hydrogenation of MDA (Run 11). This physical mixture gives a T95 of 140 min., similar to 4% Rh/Al$_2$O$_3$ and 4% Rh/TiO$_2$ catalysts. The T95 for 4% Rh/TiAl$_2$O$_5$ (TiO$_2$:Al$_2$O$_3$=1:1) catalyst is 55 min.

Superior activity and selectivity for 2% and 3%, Rh/TiAl$_2$O$_5$ (TiO$_2$:Al$_2$O$_3$ =1:1) catalyst for the hydrogenation of MDA are shown (See Run 5 and 4 of Table 2). Further, the selectivity to PACM and the by-products are not affected by the level of rhodium loading.

To determine the effect of calcination temperature a 4% Rh/TiAl$_2$O$_5$ (1:1) catalyst with a support that was calcined at 900° C. instead of 650° C. was made. The total surface area of the high temperature (900° C.) treated catalyst was 47 m$^2$/g compared to 96 m$^2$/g with the 650° C. calcined catalyst.

As shown in Table 2, the high temperature (900° C.) (Run 1 of Table 2) treated catalyst had a higher T95 of 85 min compared to 55 min with the 650° C. (Run 7 of Table 2) calcined catalyst. Further, the high temperature treatment did not change the selectivity to PACM or by-products. These results show no benefit in calcining this support beyond 650° C. The higher activity of the 650° C. calcined catalyst is believed due to its optimum surface structure defined by its total surface area and its pore size distribution.

To further investigate these catalysts, a 4% Rh/TiAl$_2$O$_5$ (1:1) catalyst was made by a different route. This support was made by first mixing liquid Ti-isopropoxide and Al-butoxide and then adding the liquid mixed metal alkoxide to a pH 9.5 aqueous NH3 solution. The precipitate was expected to have a true mixed oxide composition of Al$_2$O$_3$ and TiO$_2$. This precipitate was then dried and calcined at 650° C. As shown in Table 2, the catalyst made with this support (4% Rh/TiAl$_2$O$_5$) had very high activity (T95 - 55 min), (Run 8 of Table 2) similar to the one made with Ti isopropoxide and pseudo Boehmite.

EXAMPLE 22

The effect of alkali moderation of the catalysts for MDA hydrogenation was determined in this series of runs. Table 3 sets forth the results.

Rh/TiAl$_2$O$_5$ catalyst had a T95 of 90 min and in the second use, the catalyst activity increased to give a 50 min T95, similar to the undoped catalyst. To reduce secondary amines further, a catalyst with 4.5% LiOH was prepared and tested. With this catalyst, the secondary amines were 6% compared to 18% with the undoped catalyst. The activity in the first use with this catalyst was lower with a T95 of 180 min compared to a T95 of 55 min with the undoped catalyst.

As shown in Table 3, the activity increased in the second and third use. In the third use the T95 was 75 min with 6.5% secondary amines compared to a T95 of 55 min and 18% secondary amines for the undoped catalyst. The three MDA hydrogenations with 4% Rh/TiAl$_2$O$_5$ (1:1)-LiOH catalyst did not pulverize this catalyst. This catalyst is more attrition resistant than the TiO$_2$ supported catalysts. The higher activity of this catalyst can be used to increase reactor capacity or lower catalyst cost by lowering the rhodium loading.

EXAMPLE 23

The effect of catalyst loading in MDA was determined in accordance with the general procedure of Example 21. Table 4 sets forth the results.

TABLE 3

Hydrogenation of 50% MDA/THF at 180° C.
850 psi pressure and at a catalyst loading of 1.5 wt %

| Run | Catalyst$^b$ | Use | T95$^a$ (or TEND) (min) | Conv. (%) | PACM (%) | t/t (%) | Half PACM (%) | PACM-Secondary Amines % |
|---|---|---|---|---|---|---|---|---|
| 1. | 4% Rh/TiAl$_2$O$_5$ (1:1) (Ex 1) | 1 | 80 | 100 | 78.9 | 14.7 | 0.4 | 18.9 |
|  |  | 2 | 55 | 100 | 80.0 | 15.7 | 0.0 | 18.3 |
| 2. | 4% Rh/TiAl$_2$O$_5$ (1:1)$^c$ (Ex 9) +3% LiOH | 1 | 92 | 96 | 88.2 | 15.2 | 2.4 | 8.3 |
|  |  | 2 | 50 | 99 | 87.5 | 15.8 | 1.9 | 9.2 |
| 3. | 4% Rh/TiAl$_2$O$_5$ (1:1)$^c$ (Ex 8) +4.5% LiOH | 1 | 180 | 95 | 81.6 | 16.5 | 10.8 | 6.6 |
|  |  | 2 | 83 | 99 | 91.5 | 17.5 | 1.5 | 6.0 |
|  |  | 3 | 75 | 99 | 90.2 | 17.5 | 2.3 | 6.6 |

$^a$Same as Table 1.
$^b$Same as Table 1.
$^c$LiOH was added to the support before Rh was deposited.

As shown in Table 3, the addition of 3% LiOH dropped the level of secondary amines from 18% to 9% (Runs 1 and 2 of Table 2). The first use with the 3% LiOH doped 4%

TABLE 4

Hydrogenation of 50% MDA/THF at 180° C.
850 psi pressure at a catalyst loading of 1.5 wt %

| Run | Catalyst$^b$ | Use | T95$^a$ (or TEND) (min) | Conv. (%) | PACM (%) | t/t (%) | Half PACM (%) | PACM-Secondary Amines % |
|---|---|---|---|---|---|---|---|---|
| 1. | Rh/TiSiO$_4$ (1:1)$^c$ (Ex 15) | 1 | 250 | 99 | 68.6 | 14.1 | 2.21 | 26.7 |
| 1a. |  | 2 | 200 | 99 | 67.4 | 13.5 | 2.4 | 27.7 |

TABLE 4-continued

Hydrogenation of 50% MDA/THF at 180° C.
850 psi pressure at a catalyst loading of 1.5 wt %

| Run | Catalyst[b] | Use | T95[a] (or TEND) (min) | Conv. (%) | PACM (%) | t/t (%) | Half PACM (%) | PACM-Secondary Amines % |
|---|---|---|---|---|---|---|---|---|
| 2. | 4% Rh/TiSiO$_4$ (1:1)[d] (Ex 14) | 1 | 55 | 99 | 61.5 | 14.4 | 2.3 | 32.3 |
| 2a. | | 2 | 46 | 99 | 62.7 | 14.7 | 1.6 | 31.9 |
| 3. | 4% Rh/TiSiO$_4$ (9:1)[d] | 1 | 157 | 96 | 61.5 | 14.4 | 7.5 | 28.3 |
| 3a. | | 2 | 162 | 99 | 64.9 | 15.6 | 2.7 | 29.7 |
| 4. | 4% Rh/SiO$_2$ (Ex 17) | 2 | 330 | 100 | 68.9 | 21.7 | 0.0 | 28.6 |
| 4a. | 4% Rh/TiO$_2$ (Ex 16) | 2 | 140 | 96.0 | 74.7 | 13.6 | 8.7 | 15.6 |

[a and b]Same as Table 1.
[c]Made by mixing colloidal SiO$_2$ and Ti-isopropoxide.
[d]Made by mixing silicon ethoxide and Ti-isopropoxide.

As shown in Table 4, the 4% Rh/TiSiO$_4$ (Run 1) shows a synergism in activity compared to 4% Rh/TiO$_2$ and 4% Rh/SiO$_2$ catalysts (Run 4). The 4% Rh/TiSiO$_4$ (1/1) has the same level of activity for MDA hydrogenation as the 4% Rh/TiAl$_2$O$_5$ catalyst. The 4% Rh/TiSiO$_4$ (1/1) catalyst is at least twice as active as the commercial 4% Rh/Al$_2$O$_3$ catalyst. The secondary amines with this catalyst was very high at 32%. However, secondary amines should be suppressed by addition of LiOH.

Table 4 shows the activity of 4% Rh/TiSiO$_4$ catalysts at different SiO$_2$ to TiO$_2$ ratios. The 4% Rh/TiSiO$_4$ catalyst with a 1/9 - SiO$_2$/TiO$_2$ ratio has lower activity (T95 =160 min) than the 1/1 - SiO$_2$/TiO$_2$ supported catalyst (T95=46 min). Similar to 4% Rh/TiAl$_2$O$_5$ these 4% Rh/TiSiO$_4$ catalysts are an important class of catalysts that give very high activity towards MDA hydrogenation.

EXAMPLE 24

The procedure of Example 21 was repeated except that Rh on mixed zirconia metal catalysts were evaluated. Table 5 sets forth the results.

As shown in Table 5, these catalysts did not offer any advantage over the 4% Rh/Al$_2$O$_3$ catalyst. This catalyst had higher level of secondary amines than the catalysts made with the primary oxides.

As shown in Table 5, this catalyst, 4% Rh/ZrSiO$_4$ (50/50), shows synergism in activity towards MDA hydrogenation compared to 4% Rh/ZrO$_2$ and 4% Rh/SiO$_2$ catalyst. We reported similar results in our previous patent U.S. Pat. No. 5,026,914. Both 4% Rh/SiO$_2$ and 4% Rh/ZrO$_2$ has a T95 of about 310 min and 4% Rh/ZrSiO$_4$ has a T95 of 150 min. The level of secondary amines with this catalyst is high at 30%, but is similar to the 4% Rh/SiO$_2$ catalyst (29%). Once again this example shows the advantage of using mixed oxide supported catalysts.

What is claimed is:

1. In a process for the catalytic hydrogenation of aromatic amines to their ring hydrogenated counterparts, by contacting the aromatic amine with hydrogen in the presence of a rhodium catalyst, the improvement which comprises effecting said hydrogenation utilizing a catalyst comprising rhodium carried on a mixed metal support selected from the group consisting of TiAl$_2$O$_5$, TiSrO$_3$ and TiSiO$_4$, wherein

TABLE 5

Hydrogenation of 50% MDA/THF at 180° C.
850 psi pressure and at a catalyst loading of 1.5 wt %

| Run | Catalyst[b] | Use | T95[a] (or TEND) (min) | Conv.s (%) | PACM (%) | t/t (%) | Half PACM (%) | PACM-Secondary Amines % |
|---|---|---|---|---|---|---|---|---|
| 1. | 4% Rh/ZrO$_2$ (Ex 20) | 1 | 400 | 98 | 77.4 | 14.3 | 3.2 | 17.3 |
| 1a. | | 2 | 310 | 97 | 72.9 | 13.9 | 5.8 | 18.4 |
| 2. | 4% Rh/ZrSiO$_4$ (1:1) Ex 19 | 1 | 190 | 99 | 66.8 | 14.8 | 1.2 | 29.7 |
| 2a. | | 2 | 150 | 100 | 66.6 | 16.7 | 0.0 | 31.4 |
| 3. | 4% Rh/SiO$_2$ (Ex 17) | 1 | 460 | 100 | 69.1 | 21.5 | 0.0 | 28.5 |
| 4. | 4% Rh/ZrAl$_2$O$_5$ (1:1) Ex 18 | 1 | 180 | 97 | 65.3 | 14.3 | 6.9 | 26.2 |
| 4a. | | 2 | 120 | 100 | 69.9 | 15.5 | 0.9 | 27.5 |
| 5. | 4% Rh/Al$_2$O$_3$ | 2 | 150 | 99 | 94.3 | 17.9 | 0.7 | 4.0 |

[a]Same as Table 1.
[b]Same as Table 1.
[c]Commercial catalyst.

TiSiO$_4$ is formed by the reaction of a titanium alkoxide with a silicon alkoxide.

2. The process of claim 1 wherein the aromatic amine is represented by the formulas:

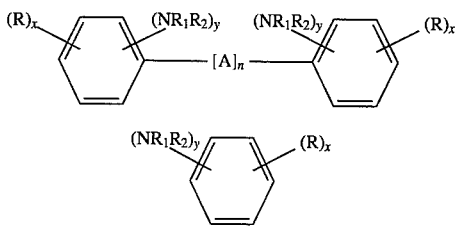

wherein R is hydrogen or C$_{1-6}$ aliphatic, R$_1$ and R$_2$ are hydrogen or C$_{1-6}$ aliphatic, A is C$_{1-4}$ alkyl, n is 0 or 1, x is 1–3 and y is 0 to 2 except the sum of the y groups in Formula I excluding A may be 1.

3. The process of claim 2 wherein said aromatic amine is represented by formula I and the mixed metal support is TiAl$_2$O$_5$ or TiSrO$_3$.

4. The process of claim 3 wherein the amount of rhodium on the mixed metal titania support ranges from about 1 to 25 parts by weight, as metal, per 100 parts mixed metal support.

5. The process of claim 4 wherein the catalyst is present in an amount from about 0.1 to 10% by weight of the aromatic amine.

6. The process of claim 5 wherein R is hydrogen, methyl, ethyl or tert-butyl.

7. The process of claim 6 wherein each y is 1.

8. The process of claim 6 wherein R$_1$ and R$_2$ are hydrogen.

9. The process of claim 7 wherein the support is TiAl$_2$O$_5$.

10. The process of claim 8 wherein the support is TiSrO$_3$.

11. The process of claim 8 wherein n is 0.

12. The process of claim 9 wherein R is hydrogen, A is —CH$_2$— and n is 1.

13. The process of claim 2 wherein said aromatic amine is represented by formula II.

14. The process of claim 13 wherein the catalyst is present in an amount from about 0.5 to 5% by weight of the aromatic amine.

15. The process of claim 14 wherein the rhodium ranges from about 1 to about 25 parts by weight, as metal, per 100 weight parts mixed metal support.

16. The process of claim 15 wherein R$_1$ and R$_2$ are hydrogen.

17. The process of claim 16 wherein R is hydrogen, methyl, ethyl, or tert-butyl and x is 1 or 2.

18. The process of claim 17 wherein y is 1 and the support is TiAl$_2$O$_5$.

19. The process of claim 2, wherein the support is TiSiO$_4$.

20. The process of claim 19 wherein the titanium alkoxide is titanium isopropoxide and the silicon alkoxide is silicon ethoxide.

* * * * *